(12) United States Patent
Rangheard et al.

(10) Patent No.: US 8,664,345 B2
(45) Date of Patent: *Mar. 4, 2014

(54) PROCESS FOR THE PREPARATION OF A CATALYST COMPOSITION FOR DIMERIZATION, CODIMERIZATION AND OLIGOMERIZATION OF OLEFINS

(75) Inventors: Claudine Rangheard, Lyons (FR); Helene Olivier-Bourbigou, Saint Genis-Laval (FR); David Proriol, Brignais (FR)

(73) Assignee: IFP Energies nouvelles, Rueil-Malmaison Cedex (FR)

( * ) Notice: Subject to any disclaimer, the term of this patent is extended or adjusted under 35 U.S.C. 154(b) by 39 days.

This patent is subject to a terminal disclaimer.

(21) Appl. No.: 13/124,525

(22) PCT Filed: Oct. 13, 2009

(86) PCT No.: PCT/FR2009/001203
§ 371 (c)(1),
(2), (4) Date: Jul. 7, 2011

(87) PCT Pub. No.: WO2010/043784
PCT Pub. Date: Apr. 22, 2010

(65) Prior Publication Data
US 2011/0263804 A1    Oct. 27, 2011

(30) Foreign Application Priority Data
Oct. 17, 2008  (FR) ...................................... 08 05745

(51) Int. Cl.
| | | |
|---|---|---|
| C08F 4/70 | (2006.01) | |
| C08F 4/80 | (2006.01) | |
| C08F 4/60 | (2006.01) | |
| B01J 31/00 | (2006.01) | |
| B01J 31/28 | (2006.01) | |

(52) U.S. Cl.
USPC ........ 526/172; 526/169.1; 526/161; 502/104; 502/103

(58) Field of Classification Search
USPC ........ 556/138; 526/172, 161, 169.1; 502/103, 502/104
See application file for complete search history.

(56) References Cited

U.S. PATENT DOCUMENTS

| 8,101,762 B2 * | 1/2012 | Rangheard et al. ............. 546/88 |
| 2011/0009581 A1 * | 1/2011 | Rangheard et al. ............ 526/172 |
| 2011/0263804 A1 * | 10/2011 | Rangheard et al. ............ 526/172 |

FOREIGN PATENT DOCUMENTS

WO    2009103877 A1    8/2009

OTHER PUBLICATIONS

Rangheard, C.; Proriol, D.; Olivier-Bourbigou, H.; Braunstein, P. Dalton Trans., 2009, 770-772.*
Jie, S.; Zhang, S.; Sun, W.-H.; Kuang, X.; Liu, T.; Guo, J. J. Mol. Catal. A: Chemical, 2007, 269, 85-96.*
Zhang, Z.Y. et al., "A novel iron catalyst for the polymerization of butadiene," Journal of Molecular Catalysis, vol. 17, 1982, pp. 65-76.
Jie, S. et al., "Iron(II) complexes ligated by 2-imino-1,10-phenanthrolines: Preparation and catalytic behavior toward ethylene oligomerization," Journal of Molecular Catalysis A: Chemical, Apr. 3, 2007, vol. 269, No. 1-2, pp. 85-96, Elsevier, Amsterdam, NL.
Rangheard, C. et al., "Direct synthesis of a new class of N,N,N ligands based on 1,2-dihydro-1,10-phenanthroline backbone and their coordination to Pd complexes," J. Chem. Soc. Dalton Translation, 2009, No. 5, Dec. 12, 2008, pp. 770-772.
International Search Report, issued on Feb. 24, 2010, in corresponding PCT/FR2009/001203.

* cited by examiner

Primary Examiner — Rip A. Lee
(74) Attorney, Agent, or Firm — Millen, White, Zelano & Branigan, P.C.

(57) ABSTRACT

This invention describes a process for the preparation of a catalytic composition that can be used for oligomerization, codimerization, or polymerization of olefins. This invention also describes the catalytic composition that can be obtained by said process for the preparation and its use for oligomerization, codimerization, or polymerization of olefins.

20 Claims, 2 Drawing Sheets

[Key to Figure 1:]

Figure 1 : Ethylene Consumed as a Function of Time (Minutes) According to Test 1 of Table 1 (Example 2)

Masse de charge (g) = Feedstock Weight (g)

[Key to Figure 2:]

Figure 2: Ethylene Consumed as a Function of Time (Minutes) According to the Comparison Test (Example 3)

Charge (g) = Feedstock (g)

Masse de charge (g) = f (tps)  =  Feedstock Weight (g) = f (tps)

Temps (min) = Time (Minutes)

PROCESS FOR THE PREPARATION OF A CATALYST COMPOSITION FOR DIMERIZATION, CODIMERIZATION AND OLIGOMERIZATION OF OLEFINS

FIELD OF THE INVENTION

This invention describes a process for manufacturing a catalytic composition that can be used for oligomerization, codimerization or polymerization of olefins.

This invention also describes the catalytic composition that can be obtained by said preparation process and its use for oligomerization, codimerization or polymerization of olefins.

PRIOR ART

The linear α-olefins, especially those that contain 4 to 20 carbon atoms, have varied openings as a function of the length of their carbon chain. For example, the $C_4$ to $C_8$ olefins are primarily used as comonomers for the manufacturing of low-density polyethylenes (LLDPE); the $C_8^=$ to $C_{14}$ olefins are used as intermediaries in the industry of lubricants; and the $C_{10}$-$C_{18}$ olefins are used for the manufacturing of detergents. These olefins undergo a strong economic growth. Most of the industrial processes for production of α-olefins are processes for oligomerization of ethylene catalyzed by complexes of transition metals (Ni, Ti, Zr) or $AlEt_3$ (Alpha Olefins Applications Handbook, G. R. Lapin and J. D. Sauer Eds M. Dekker, NY, 1989). Most of these processes lead to Schulz-Flory-type distributions that can be quantified by the value K. This value K represents the probability of chain propagation and is experimentally determined by the molar ratio $C_{n+2}/C_n$. The values of K that are encountered in the industrial processes are on the order of 0.7-0.8, which corresponds to broad distributions of α-olefins that range from $C_4$ to $C_{20}^+$. It is then difficult to upgrade all of the products that are formed, in particular the "waxes" (olefins>C30).

In contrast, significant quantities of branched or internal olefins can also be produced by these processes: olefins that are often difficult to separate and that are undesirable for the industrial processes. It is therefore important to develop new processes that make it possible to minimize these olefins.

For several years, continuous research has been underway to find new catalytic systems that make it possible to access more narrow olefin distributions, for example that make it possible to optimize the formation of $C_4$-$C_{10}$, which are more selective in linear alpha-olefins and more active.

Relatively recently, the catalytic systems that comprise transition metals of the groups 8-10, such as iron, nickel, palladium and cobalt combined with diimine-type chelate ligands, have been developed and applied for the polymerization of ethylene or the copolymerization of alpha-olefins or olefins that carry one function, such as methyl acrylate (see, for example, the review by V. Gibson in Angew. [Applied] Chem. Int. Ed. 1999, 38, 429). These systems most often implement a co-catalyst that is a derivative of the aluminum such as an aluminoxane.

It was more recently shown (S. Svejda et Coll., Organometallics, 1999, 18, 65-74; WO-A-96/2310; WO-A-00/10945; and U.S. Pat. No. 5,880,323) that the systems that comprise a complex of nickel combined with an α-diimine-type ligand in the presence of a Lewis acid or a Bronsted acid, but more particularly an aluminum derivative such as an aluminoxane or an alkylaluminum chloride, made it possible to catalyze the oligomerization of the ethylene into linear α-olefins. However, in these systems, the quantities of aluminoxane that are used are generally high (more than 100 equivalents per mol of nickel), and the distribution of the olefins that are formed is broad: from C4 to C20, with a Schulz-Flory constant that is generally higher than 0.6.

It was also shown that certain iron complexes, combined with bis(imino)pyridine-type trident chelate ligands, activated by an alkyl derivative of aluminum and more particularly an aluminoxane, catalyze the oligomerization of ethylene (see the review by V. Gibson, Chem. Rev. 2007, 107, 1745; Du Pont de Nemours WO99/02472; WO 02/06192 A1; Britovek et al., Chem. Eur. J., 2000, 6, 12, pp. 2221-2231, BP Chemicals WO 99112981; Chevron Phillips WO2005/080301A1).

The distribution of the formed oligomers essentially depends on the nature of the bis(imino)pyridine ligand, in particular substituents that are found on the aromatic cores of imines. These distributions in general follow a Schulz-Flory-type law whose characteristic factor K varies from 0.70 to 0.85 (M. Brookhart, B. Small, J. Am. Chem. Soc. 1998, 120, 7143-7144).

Shell International Research (WO 01/58874 A1; WO 02/00339 A2, WO 2004/037415 A2; WO 2007/059015) teaches that the use of asymmetrical bis-arylimine pyridine ligands combined with iron complexes that are activated by an aluminoxane makes it possible to access linear Schulz-Flory olefin distributions (no deviation) with a minimization of the production of high-mass products.

In its patent application US 2005/0192470, Exxon Mobil describes a process for producing linear α-olefins whose chain length does not exceed 12 carbon atoms (short Schulz-Flory distribution K=0.45) using the implementation of the 2,6-bis(phenylimino)-pyridyl ligand that is combined with a metal preferably of iron (II) and an aluminoxane.

These complexes, which carry the bis-arylimine pyridine ligands that take up very little space, lead to the shortest oligomer distributions. However, they include the drawback of being not very stable and they deactivate quickly, particularly with temperature, leading in particular to the formation of polymers and waxes.

We discovered, surprisingly enough, that when the nitrogen-containing organic ligands of general formula A, described below, were brought into the presence of a base, and then into the presence of an iron (III) compound, new precursors of catalysts for oligomerization, codimerization or polymerization of olefins that do not include the drawbacks of the systems described above were obtained.

SUMMARY OF THE INVENTION

This invention describes a process for the preparation of a catalytic composition that can be used for oligomerization, codimerization, or polymerization of olefins implementing at least one nitrogen-containing organic compound of general formula A, at least one base, at least one iron (III) compound, and at least one activator.

This invention also describes the catalytic composition that can be obtained by said preparation process and its use for the oligomerization, codimerization or polymerization of olefins.

DETAILED DESCRIPTION OF THE INVENTION

This invention describes a process for the preparation of a catalytic composition that comprises the following stages:
a) Bringing into contact, optionally in the presence of a solvent, at least one nitrogen-containing organic compound of general formula A, described below, with at least one base (compound B)

Compound of Formula A where $R_2$ to $R_{10}$, identical or different, are selected from among hydrogen; optionally substituted, aryl or aralkyl, cycloalkyl or aromatic hydrocarbyl groups that may or may not be saturated; and alkoxy, aryloxy, or amino groups, or halide,
b) Bringing into contact, optionally in the presence of a solvent, the product of the reaction that is performed in stage a) with an iron (III) precursor (compound C),
c) Optionally isolation from at least one of the products that is obtained during stage b),
d) Addition of an activating agent (compound D),
e) Optionally addition of a solvent (compound E).

The thus obtained composition has a good catalytic activity, in particular prolonged activities particularly at temperatures that range up to 80-100° C. It also makes it possible to minimize the quantity of sub-products obtained, in particular to reduce the quantity of polymers and waxes relative to the known catalytic compositions of the prior art.

This invention also describes a process for oligomerization, codimerization or polymerization that implements said catalytic compositions.

Description of Stage a)

Nitrogen-Containing Organic Compound A

The nitrogen-containing organic compound A has the following general formula:

Compound of General Formula A in which $R_2$ to $R_{10}$, identical or different, are selected from among hydrogen; optionally substituted, aryl or aralkyl, cycloalkyl or aromatic hydrocarbyl groups that may or may not be saturated; and alkoxy, aryloxy, or amino groups, or a halide.

In the compounds of general formula A, the groups $R_2$ to $R_{10}$, identical or different, can also represent organic radicals in which one or more hydrogen atoms are replaced by halides, for example, a fluoride, or groups comprising at least one heteroatom such as an oxygen, a nitrogen, a sulfur, phosphorus or a silicon. These heteroelements can be contained in aromatic or saturated or unsaturated alkyl cycles.

Two adjacent radicals among the groups $R_2$-$R_5$ or $R_6$-$R_{10}$ can form cycles.

By way of examples of compounds of general formula A, it is possible to cite:

The compounds of general formula A are obtained by reacting, preferably in a solvent, a compound X that belongs to the family of substituted pyridines that comprise at least one ketone function, with a compound Y that belongs to the family of amino-quinolines and their derivatives.

The compound Y belongs to the family of amino-quinolines and their derivatives. The corresponding general formula is written below:

General Formula of Compound Y

The compound X corresponds to the following general formula:

General Formula of Compound X with $R_2$ to $R_{10}$, identical or different, are [sic] selected from among hydrogen; optionally substituted, aryl or aralkyl, cycloalkyl or aromatic hydrocarbyl groups that may or may not be saturated; alkoxy, aryloxy, or amino groups, or halides.

The compound X is, for example, 2-acetylpyridine, 4-methyl-2-acetylpyridine, 6-bromo-2-acetylpyridine, 6-methyl-2-acetylpyridine, or 6-methoxy-2-acetylpyridine.

The compound Y is, for example, 8-aminoquinoline, or the 2-methyl-8-aminoquinoline.

The reaction between the two compounds X and Y is preferably performed in a solvent, at a temperature of preferably between 20 and 250° C. The compounds X and Y can be introduced in any order.

Among the organic solvents that can be used for the reaction between the two compounds X and Y, it is possible to cite the conventional organic solvents that are polar or apolar, protic or aprotic, such as the aromatic or aliphatic hydrocarbons such as toluene, xylene, cyclohexane, pentane, hexane or heptane; the chlorinated solvents such as dichloromethane; the nitrated solvents such as acetonitrile; the oxidized solvents such as acetone, tetrahydrofuran, diethyl ether, dimethyl sulfoxide (DMSO) and dimethylformamide (DMF); or the alcohols such as methanol or ethanol.

In a preferred manner, the solvents that are used are aprotic polar solvents.

These solvents can be used alone or in a mixture. They are preferably dried, by distillation or by being run over an adsorbent, before being used.

The reaction of X with Y is preferably performed in the presence of a catalyst. The catalysts are preferably selected from among the Bronsted acids or the Lewis acids.

The Bronsted acids are of the $H^+X^-$ type, in which $X^-$ represents an anion. The $X^-$ anions are preferably selected from among the following anions: tetrafluoroborates, tetraalkylborates, hexafluorophosphates, hexafluoroantimonates, alkylsulfonates (for example, methyl sulfonate), p-toluenesulfonates, perfluorosulfonates (for example, trifluoromethylsulfonate), fluorosulfonates, sulfates, phosphates, perfluoroacetates (for example, trifluoroacetate), perfluorosulfonamides (for example, bis-trifluoromethanesulfonyl amide of formula $N(CF_3SO_2)_2^-$), fluorosulfonamides, perfluorosulfomethides (for example, the tris-trifluoromethanesulfonyl methylide of formula $C(CF_3SO_2)_3^-$), carboranes, tetraphenylborates and the tetraphenylborate anions whose aromatic cores are substituted.

The Lewis acids are by definition compounds that can accept an electron doublet.

By way of example, it is possible to cite the triflates of lanthanides, in particular ytterbium triflate ($Yb(OTf)_3$), and scandium triflate.

The reaction between X and Y can optionally be performed in the presence of iodine.

The molar ratio between the compound X and the compound Y is between 10 and 0.1.

Compound B: Base

All of the bases that are able to eliminate a proton (N—H) from the ligand of general formula A can be used.

The base can be organic or inorganic.

By way of examples, it is possible to cite cesium carbonate, potassium carbonate, sodium carbonate or calcium carbonate ($Cs_2CO_3$, $K_2CO_3$, $Na_2CO_3$, $CaCO_3$), $K_3PO_4$, NaOAc (Ac=acetate), butyl lithium (BuLi), sodium hydride (NaH), $KN(SiMe_3)_2$ (or KHMDS, the potassium bis(trimethylsilyl) amide), $NaN(SiMe_3)_2$ or $LiN(is-Pr)_2$ (is-Pr=isopropyl).

Bringing the base (compound B) into contact with the compound of general formula A can be done at a temperature that is between −100° C. and +100° C., preferably between −78° C. and 50° C.

This contact stage can be performed in the presence of a solvent.

The solvents that are used during the stage a) for bringing the base into contact with the compound of general formula A are selected from among the polar or apolar conventional organic solvents, such as the aromatic or aliphatic hydrocarbons such as toluene, xylene, cyclohexane, pentane, hexane or heptane; the chlorinated solvents such as dichloromethane; the nitrated solvents such as acetonitrile; or the oxidized solvents such as acetone, tetrahydrofuran, diethyl ether, dimethyl sulfoxide (DMSO) and dimethylformamide (DMF).

These solvents can be used alone or in a mixture. They are preferably dried by distillation or by being run over an adsorbent before being used.

The molar ratio between the base (compound B) and the compound of general formula A is between 10 and 0.5, preferably between 5 and 1.

As an example of the intermediate compound that can be formed during stage a), it is possible to cite the anionic ligands of general formula:

in which $R_2$ to $R_{10}$, identical or different, are selected from among hydrogen; optionally substituted, aryl or aralkyl, cycloalkyl or aromatic hydrocarbyl groups that may or may not be saturated; and alkoxy, aryloxy, or amino groups, or halide.

Description of Stage b): Bringing the Product of the Reaction Obtained in Stage a) into Contact with the Iron (III) Precursor (Compound C)

Compound C: Iron (III) Precursor:

The iron compounds used in the process according to this invention are iron compounds of valence 3. They can be selected from among the metal halides such as the iodides, the bromides or the chlorides or else the nitrates, the sulfates, the amidinates, the carboxylates, such as the acetates, the triflates, the oxalates, and the diketonates. It is also possible to use organometallic compounds or metal hydrides.

The compound C can have a monomeric, dimeric or oligomeric nature of a higher order.

The adducts of the metal compounds with a Lewis base can also be used according to this invention. Among the Lewis bases that can be used according to this invention, it is possible to cite ethers, amines, thioethers and phosphines.

Among the examples of type C compounds that can be used according to this invention, it is possible to cite: $FeCl_3$; $FeCl_3$, $xH_2O$; $FeBr_3$; $Fe(CH_3COCH=C(O)CH_3)_3$, $Fe(NSiMe_3)_3$; $Fe(NO_3)_3$; $xH_2O$; $Fe_2(SO_4)_3$, $xH_2O$.

The mixture of the product resulting from stage a) and the iron compound C can be produced in any order, preferably in a solvent.

Among the organic solvents that can be used in stage b), it is possible to cite the polar or apolar conventional organic solvents, such as the aromatic or aliphatic hydrocarbons such as toluene, xylene, cyclohexane, pentane, hexane or heptane; the chlorinated solvents such as dichloromethane; the nitrated solvents such as acetonitrile; or the oxidized solvents such as acetone, tetrahydrofuran, diethyl ether, dimethyl sulfoxide (DMSO) and dimethylformamide (DMF).

These solvents can be used alone or in a mixture.

The organic solvent will preferably be selected in such a way as to dissolve the mixture of the two compounds.

The same solvent as the one used in stage a) will preferably be used.

Description of Stage c) for Isolating at Least One of the Products Obtained from Stage b):

This stage is optional. The isolation of at least one of the products obtained from stage b) can be done by evaporation of the solvent of the reaction that is used in this stage b), followed by washing the product(s) obtained; or by precipitation or by crystallization.

Description of Stage d): Addition of the Activating Agent (Compound D)

The activating agent (compound D) can be defined as any radical that can form a metal-carbon or metal-hydrogen bond.

If the iron compound C already contains at least one metal-carbon bond, the activating agent can be a Lewis acid, a Bronsted acid, or an alkylating agent or any compound that can perform the hydrogenolysis of a metal-carbon bond.

Preferably, the activating agent is selected from among the derivatives of the aluminum such as, for example, the aluminoxanes, the organoaluminums, the aluminum halides, the aluminates; the boron derivatives such as, for example, boranes or borates; or the derivatives of zinc such as, for example, the organozincs.

By way of example, the organoaluminums that can be used as activators in the process for the preparation of the catalytic composition according to the invention have general formula $AlR_nX'_{(3-n)}$ with n between 1 and 3; with the groups R, identical or different, being selected from among the alkyl, aryl or aralkyl groups that have 1 to 12 carbon atoms; and with X', identical or different, being selected from among the halides, the alkoxy, the aryloxy, the amides or the carboxylates. The organoaluminums will preferably be selected from the group of trialkylaluminums or from the group of dialkylaluminum chlorides, or from the group of alkylaluminum dichlorides.

The aluminoxanes that can be used as activators in the catalytic composition are selected from among the alkylaluminoxanes such as methylaluminoxane (MAO) or ethylaluminoxane (EAO) or from among the modified alkylaluminoxanes such as modified methylaluminoxane (MMAO).

According to the process of this invention, the molar ratio between the compound D (activator) and the compound C (iron) is between 1 and 10,000, preferably between 1 and 1,000, and even more preferably between 1 and 200.

Description of Stage e): Addition of the Solvent (E):

The organic solvent that is used during stage e) is preferably an aprotic solvent. Among the solvents that can be used in the process according to this invention, it is possible to cite hydrocarbons such as pentane, hexane, cyclohexane or heptane; aromatic hydrocarbons such as benzene, toluene or xylenes; chlorinated solvents such as dichloromethane or chlorobenzene; or else acetonitrile, diethyl ether, and tetrahydrofuran (THF). The organic solvent will preferably be a saturated or unsaturated aliphatic solvent or an aromatic hydrocarbon.

Catalytic Process of Oligomerization, Codimerization or Polymerization

The catalytic composition that can be prepared according to the process of this invention can be used for the dimerization, the codimerization, the oligomerization or the polymerization of olefins.

The olefins that can be transformed by the catalytic compositions according to the invention are more particularly ethylene, propylene, n-butenes and n-pentenes, alone or in a mixture (codimerization), pure or diluted by an alkane, as they are found in "fractions" obtained from petroleum refining processes, such as catalytic cracking, steam cracking, or else in the fractions that are obtained from the Fischer-Tropsch-type processes.

The catalytic reaction for transformation of olefins can be conducted in a closed system, a semi-open system or continuously, with one or more reaction stages. Vigorous stirring is to ensure good contact between the reagent(s) and the catalytic composition.

The reaction temperature can be −40 to +250° C., preferably 0° C. to +150° C.

The heat generated by the reaction can be eliminated by any means that are known to one skilled in the art.

The pressure can vary from the atmospheric pressure at 20 MPa, preferably the atmospheric pressure at 10 MPa.

EXAMPLES

Example 1

Process for the Preparation of the Catalytic Composition According to the Invention Description of Stage a)

Compound A1

0.9 ml of nBuLi (1.44 mmol, 1.6 M in hexane) is added to a solution of 504 mg of the compound A1 (1.44 mmol) in 10 ml of anhydrous THF at −78° C. The orangey-red solution that is obtained is stirred until it has been at ambient temperature for 1 hour.

Description of Stage b)

A solution of 234 mg of $FeCl_3$ (1.44 mmol) in 10 ml of anhydrous THF is added drop by drop to the reaction medium that is obtained at the end of stage a). The reaction medium becomes violet. The mixture is stirred for 4 hours at ambient temperature. The reaction medium is then concentrated by putting the pump under vacuum. 15 ml of pentane is then added. A solid precipitates. The higher liquid phase is separated using a cannula, and then the precipitate is washed with pentane (2×10 ml). 472 mg of a dark violet powder is obtained, which corresponds to a yield of 70% by weight.

The thus obtained iron complex is characterized by IR (characteristic IR bands: 3059, 2957, 2870, 1603, 1585, 1566, 1495, 1451, 1390, 1325, 1126, 1047, 1020, 827, 778, 754 $cm^{-1}$) and by mass spectroscopy.

The characteristic band of the N—H bond has disappeared.

| Empirical Formula | Theoretical Mass | Measured Mass |
|---|---|---|
| $C_{23}H_{18}Cl_2N_4Fe$ | 476.0253 | 476.0299 |

Example 2

Catalytic Test that Uses the Catalytic Composition According to this Invention

The catalytic test is implemented in a Grignard-type reactor with a 250 ml capacity that is equipped with a double jacket and a bar magnet. Before the reaction, the reactor is placed under vacuum (approximately $6.10^{-2}$ mbar) and heated at 90° C. for 4 hours. After cooling at ambient temperature, the reactor is pressurized at 3.5 MPa of ethylene (0.5 MPa above the test pressure provided) to test its seal for one entire night. The reactor is then heated to 80° C. Under 0.05 MPa of ethylene, the following are introduced into the reactor: 42.4 ml of distilled toluene and then the MAO solution in the toluene (10% in toluene, 200 equivalents, 2.6 ml), and then the catalytic solution ($2.10^{-5}$ mol of iron complex in 5 ml of toluene).

Figure 1:
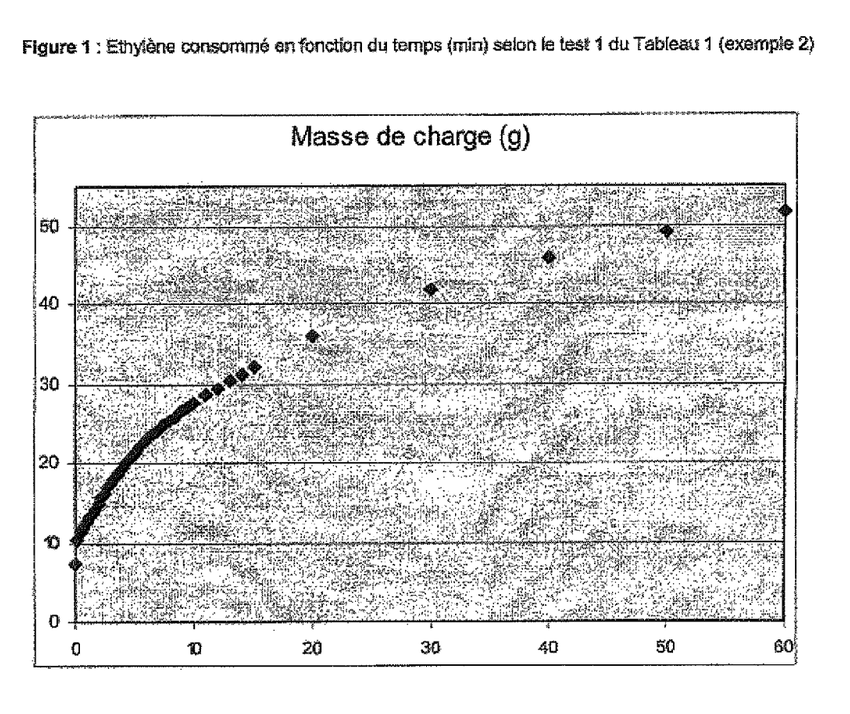
FIGS. 1 and 2 show the consumption by weight of ethylene measured as a function of time. This consumption is representative of the activity of the catalytic system.
Figure 2:
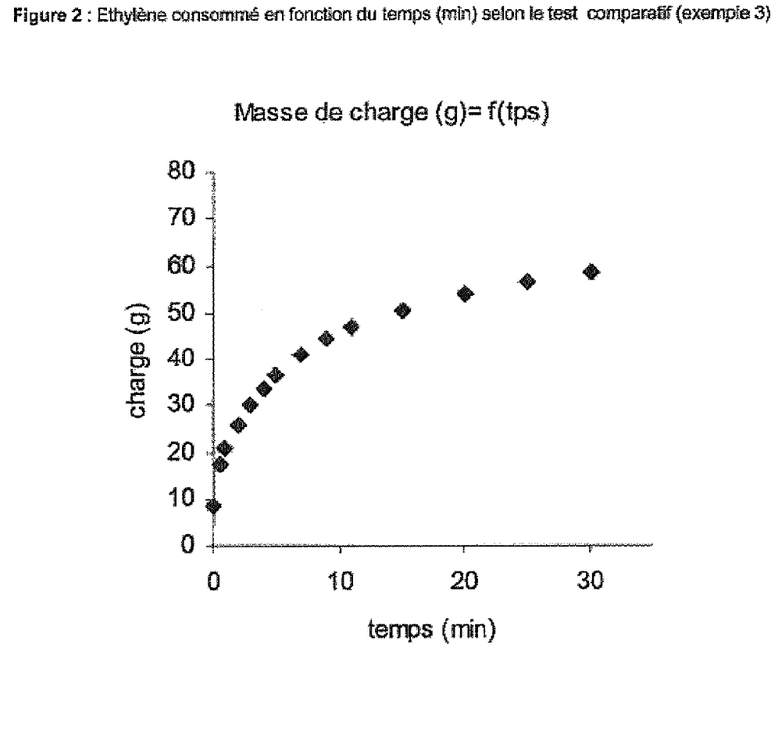

The reactor is put under 3 MPa of ethylene pressure. The ethylene pressure is kept constant during the test, the monitoring of the ethylene input being done by a pressure regulator that is connected to a ballast deposited on a scale. The activity of the catalyst corresponds to the consumption of ethylene measured by the loss of weight of the ballast connected to the reactor and containing the ethylene. The consumption of ethylene is measured as a function of time (see attached curves in the figures). It provides an indication on the catalytic activity and the stability of the catalyst over time.

At the end of the reaction, the reactor is depressurized. The gas volume is measured by a gas counter and analyzed. The liquid phase is drawn off, weighed, and the catalyst is neutralized by adding ethanol. After "trap-to-trap" vacuum distillation, the liquid phase is analyzed by gas phase chromatography. A complete balance is drawn up (input material, output material on the gas, the liquid and optionally the solid).

TABLE 1

Al/Fe: 200 equivalents, Fe: 2 · 10⁻⁵ mol, Toluene 50 ml, P: 30 bar, T: 80° C.,
Test Period: 60 minutes. MAO: Aldrich, 10% in Toluene
α = Percent of Linear alpha-Olefins Contained in the Corresponding Fraction

| Precursor of Fe | g/g of Fe·h⁻¹ | C$_4$ % by Weight | C$_4$ α | C$_6$ % by Weight | C$_6$ α | C$_8$ % by Weight | C$_8$ % α | C$_{10}$ % by Weight | C$_{10}$ % α | C$_{12}$ % by Weight | C$_{12}$ % α | PE + Waxes |
|---|---|---|---|---|---|---|---|---|---|---|---|---|
| Test 1 Precursor of the Fe Prepared According to Example 1 (Stage b) | 30950 | 53.7 | 92.1 | 24.1 | 73.9 | 9.7 | 68.6 | 3.9 | 63.4 | 0.4 | — | 8 |

The consumption of ethylene measured as a function of time (minutes) according to the Catalytic Test 1 is shown in FIG. 1.

Example 3

Catalytic Test Implemented with a Complex According to the Prior Art

The catalytic test is implemented with the bis-imino-pyridine complex that is described below. The complex that is used is an iron (II) complex and not an iron (III) complex as in the catalytic composition according to this invention.

TABLE 2

Al/Fe: 200 equivalents, Fe: 2 · 10⁻⁵ mol, Toluene 50 ml, P: 30 bar,
T: 80° C., Test Period: 30 minutes. MAO: Aldrich, 10% in Toluene
α = Percent of Linear alpha-Olefins Contained in the Corresponding Fraction

| Precursor of Fe | C$_4$ % by Weight | C$_4$ α | C$_6$ % by Weight | C$_6$ α | C$_8$ % by Weight | C$_8$ % α | C$_{10}$ % by Weight | C$_{10}$ % α | C$_{12}$ % by Weight | C$_{12}$ % α | PE + Waxes |
|---|---|---|---|---|---|---|---|---|---|---|---|
| Test 2 Precursor of the Fe Prepared According to the Prior Art | 9.4 | 93.9 | 10.7 | 98.5 | 8.4 | 98.3 | 2.1 | 96.24 | 0.2 | 100 | 69 |

It is observed that the polymer mass that is produced is very significant: 69% of the products formed. Furthermore, if the curve that describes the consumed ethylene mass as a function of time (FIG. 2) is considered, it can be noted that after the first 10 minutes, the system deactivates very quickly.

The invention claimed is:

1. A process for the preparation of a catalytic composition, said process comprising:
   a) contacting optionally in the presence of a solvent, at least one nitrogen-containing organic compound of formula A with at least one base (compound B)

Compound of Formula A where $R_2$ to $R_{10}$, identical or different, are hydrogen; optionally substituted aryl or aralkyl, cycloalkyl or aromatic hydrocarbyl groups; alkoxy, aryloxy, or amino groups, or a halide, b) contacting optionally in the presence of a solvent, a product of the reaction that is obtained in a) with an iron (Ill) precursor compound C, c) isolating at least one product obtained during b), d) adding an activating agent compound D, and e) optionally adding a solvent (compound E).

2. The process according to claim 1, wherein $R_2$ to $R_{10}$, which may be identical or different, are optionally substituted aryl or aralkyl, cycloalkyl or aromatic hydrocarbyl groups; or alkoxy, aryloxy, or amino groups, in which one or more hydrogen atoms are replaced by halides, or aromatic or saturated or unsaturated alkyl cycles in which at least one heteroatom is present.

3. The process according to claim 1, in which said base compound B is an inorganic base.

4. The process according to claim 1, wherein the molar ratio between the base compound B and the compound of formula A is between 10 and 0.5.

5. The process according to claim 1, wherein a) is performed at a temperature of between −100° C. and +100° C.

6. The process according to claim 1, wherein solvent in a) is an aromatic or aliphatic hydrocarbon; a chlorinated solvent, nitrated solvent; or an oxidized solvent used alone or in a mixture.

7. The process according to claim 1, wherein said iron precursor compound is a metal halide; a nitrate, a sulfate, an amidinate; a carboxylate, a triflate, an oxalate, a diketonate, an organometallic compound or a metal hydride.

8. The process according to claim 1, wherein the solvent in b) is an aromatic or aliphatic hydrocarbon a chlorinated solvent a nitrated solvent or an oxidized solvent, used alone or in a mixture.

9. The process according to claim 1, wherein the isolation of one of the products that is obtained during c) is performed by evaporation of the solvent and then washing of the product (s) obtained or by precipitation or by crystallization.

10. The process according to claim 1, wherein the activating agent compound D that is added during d) is a Lewis acid, a Bronsted acid, an alkylating agent, or a compound that can form a metal-carbon or hydrogen metal bond.

11. The process according to claim 1, wherein said activating agent compound D is a derivative of aluminum, a boron derivative or a derivative of zinc.

12. The process according to claim 11, wherein the activating agent is an organoaluminum of formula $AlR_nX'_{(3-n)}$ with n of 1 to 3, each R, identical or different, are alkyl, aryl or aralkyl groups that have 1 to 12 carbon atoms; and X', identical or different, are halides, alkoxy, aryloxy, amides or carboxylates.

13. The process according to claim 1, wherein the molar ratio between the activating agent compound D and the iron precursor compound C is between 1 and 10,000.

14. The process according to claim 1, wherein the solvent in e) is an aprotic solvent that is a hydrocarbon, an aromatic hydrocarbon, a chlorinated solvent acetonitrile, diethyl ether, or tetrahydrofuran (THF).

15. A catalytic composition prepared according to the process of claim 1.

16. A process for dimerization, codimerization, oligomerization or polymerization of olefins comprising subjecting the olefins to the catalytic composition according to claim 15.

17. The process according to claim 1, wherein $R_2$ to $R_{10}$ are independently a group containing oxygen, nitrogen, sulfur or silicon in an aromatic or saturated or unsaturated alkyl cycle.

18. The process according to claim 1, wherein compound B is cesium carbonate, potassium carbonate, sodium carbonate or calcium carbonate ($Cs_2CO_3$, $K_2CO_3$, $Na_2CO_3$, $CaCO_3$), $K_3PO_4$, NaOAc (Ac=acetate), butyl lithium (BuLi), sodium hydride (NaH), $KN(SiMe_3)_2$, KHMDS (potassium bis(trimethylsilyl) amide), $NaN(SiMe_3)_2$ or $LiN(i-Pr)_2$.

19. The process according to claim 10, wherein the solvent is toluene, xylene, cyclohexane, pentane, hexane, heptane, dichloromethane, acetonitrile, acetone, tetrahydrofuran, diethyl ether, dimethyl sulfoxide (DMSO) or dimethylformamide (DMF), used alone or in a mixture.

20. The process according to claim 10, wherein the activating agent is an aluminoxane, an organo aluminum, an aluminum halide, an aluminate, a borane, a borate, or an organozinc.

* * * * *

UNITED STATES PATENT AND TRADEMARK OFFICE
CERTIFICATE OF CORRECTION

PATENT NO. : 8,664,345 B2  
APPLICATION NO. : 13/124525  
DATED : March 4, 2014  
INVENTOR(S) : Rangheard et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 120 days.

Signed and Sealed this

Twenty-ninth Day of September, 2015

Michelle K. Lee  
*Director of the United States Patent and Trademark Office*